United States Patent
Goslin (10) Patent No.: US 10,987,594 B2
(45) Date of Patent: Apr. 27, 2021

(54) SYSTEMS AND METHODS TO ELICIT PHYSICAL ACTIVITY IN USERS ACTING AS CARETAKERS OF PHYSICAL OBJECTS

(71) Applicant: Disney Enterprises, Inc., Burbank, CA (US)

(72) Inventor: Michael P. Goslin, Los Angeles, CA (US)

(73) Assignee: Disney Enterprises, Inc., Burbank, CA (US)

( * ) Notice: Subject to any disclaimer, the term of this patent is extended or adjusted under 35 U.S.C. 154(b) by 0 days.

(21) Appl. No.: 16/284,863

(22) Filed: Feb. 25, 2019

(65) Prior Publication Data

US 2020/0269142 A1    Aug. 27, 2020

(51) Int. Cl.
| | | |
|---|---|---|
| A63F 13/212 | (2014.01) | |
| A63F 13/825 | (2014.01) | |
| G16H 20/30 | (2018.01) | |
| A63F 13/216 | (2014.01) | |
| A63F 13/211 | (2014.01) | |
| A63F 13/69 | (2014.01) | |
| A63F 13/95 | (2014.01) | |

(52) U.S. Cl.
CPC .......... *A63F 13/825* (2014.09); *A63F 13/211* (2014.09); *A63F 13/212* (2014.09); *A63F 13/216* (2014.09); *A63F 13/69* (2014.09); *G16H 20/30* (2018.01); *A63F 13/95* (2014.09)

(58) Field of Classification Search
CPC ........ A63F 13/211; A63F 13/69; A63F 13/12; A63F 13/21; A63F 13/825; A63F 13/92; A63F 13/95; A63F 13/216; A63F 13/5375; A63F 13/60; A63F 13/65; A63F 13/212; A63F 13/816; A63F 2300/208; A63F 2300/5546; A63B 2024/0096; A63B 2071/0638; A63B 71/0622; A63B 2024/0078; G06T 19/006; A61B 5/024; G07F 17/3206; G07F 17/323; G07F 17/3262
See application file for complete search history.

(56) References Cited

U.S. PATENT DOCUMENTS

| | | | |
|---|---|---|---|
| 6,705,972 B1 * | 3/2004 | Takano | ................. A63B 24/00 482/7 |
| 6,901,390 B2 | 5/2005 | Mizokawa | |
| 7,980,997 B2 * | 7/2011 | Thukral | ............ A63B 24/0059 463/1 |

(Continued)

OTHER PUBLICATIONS

Rollycat is Always Active, Just Like your Cat, (Mar. 2016); retrieved from http://rollycat.com/.

(Continued)

*Primary Examiner* — Justin L Myhr
(74) *Attorney, Agent, or Firm* — Esplin & Associates, PC (57) ABSTRACT

Systems and methods to elicit physical activity in users acting as caretakers of physical objects. Caretaking information for a physical object may define a set of caretaking criteria of a physical object. Individual caretaking criteria may comprise one or more caretaking requirements of the physical object to be satisfied based on physical activity of a user. The caretaking requirements of the physical object may "trick" the user into performing fitness/wellness behavior. In caring for the physical object, the user may actually be caring for themselves.

16 Claims, 4 Drawing Sheets

(56) References Cited

U.S. PATENT DOCUMENTS

| | | | |
|---|---|---|---|
| 8,235,724 B2 | 8/2012 | Gilley | |
| 9,390,626 B1 | 7/2016 | Horowitz | |
| 9,814,993 B2 | 11/2017 | Ponomarev | |
| 2008/0027673 A1* | 1/2008 | Trumm | A63F 13/28 702/160 |
| 2008/0051919 A1* | 2/2008 | Sakai | A63B 71/00 700/94 |
| 2009/0030977 A1* | 1/2009 | Brown | A63H 3/28 709/203 |
| 2009/0095663 A1 | 4/2009 | Stein | |
| 2012/0215328 A1* | 8/2012 | Schmelzer | G06F 19/3481 700/91 |
| 2014/0273717 A1* | 9/2014 | Judkins | A63H 3/28 446/175 |
| 2015/0050972 A1* | 2/2015 | Sarrafzadeh | A63F 13/212 463/7 |
| 2015/0056588 A1* | 2/2015 | Bayer | G09B 5/04 434/236 |
| 2015/0065213 A1* | 3/2015 | Dugan | A63F 13/52 463/7 |
| 2016/0029962 A1 | 2/2016 | Hyde | |
| 2016/0228745 A1* | 8/2016 | Rous | A61B 5/6898 |
| 2016/0325180 A1* | 11/2016 | Nelson | A63F 13/355 |
| 2017/0087726 A1* | 3/2017 | Gnana | A61B 5/0002 |
| 2017/0216675 A1* | 8/2017 | Goslin | G06T 19/006 |
| 2019/0069518 A1* | 3/2019 | Falbaum | A01K 15/025 |

OTHER PUBLICATIONS

Buzzfeed, Gays Vs. Lesbians: Raising A Robot Baby (Oct. 10, 2016); retrieved from https://www.youtube.com/watch?v=DekyZc8i7Uo.

Breazeal et al., Infant-like Social Interactions between a Robot and a Human Caretaker, Massachusetts Institute of Technology, 1998, retrieved from https://pdfs.semanticscholar.org/ddb5/2c6ed2e31ad81307a9fc9e497d7566a307a9.pdf.

\* cited by examiner

SYSTEMS AND METHODS TO ELICIT PHYSICAL ACTIVITY IN USERS ACTING AS CARETAKERS OF PHYSICAL OBJECTS

FIELD OF THE DISCLOSURE

The present disclosure relates to systems and methods to elicit physical activity in users acting as caretakers of physical objects.

BACKGROUND

There are fitness applications and devices that allow a user to track their fitness goals and activity. However, a user can easily ignore reminders to workout, and eventually they may give up their workout regimen entirely.

SUMMARY

Aspects of the present disclosure relate to systems and methods configured to elicit physical activity in users acting as caretakers of physical objects. A physical object may take the form of a toy who needs to be taken care of. The physical object may provide output conveying caretaking requirements for its well-being. The caretaking requirements of the physical object may "trick" the user into performing fitness/wellness behavior in order to satisfying the caretaking requirements even though the caretaking requirements may be unrelated to the fitness/wellness behavior itself. Accordingly, in caring for the physical object, the user may actually be caring for themselves.

The system may include one or more of non-transitory electronic storage, one or more processors configured by machine-readable instructions, and/or other components. The non-transitory electronic storage and/or one or more processors configured may be included in and/or coupled with a physical object. Other physical objects may be similarly configured. The non-transitory electronic storage may be configured to store caretaking information and/or other information.

The caretaking information for the physical object may define a set of caretaking criteria of the physical object. The individual caretaking criteria may comprise one or more caretaking requirements of the individual physical object to be satisfied based on physical activity of a user. By way of non-limiting illustration, the set of caretaking criteria may include a first criterion and/or other criteria.

The machine-readable instructions may include one or more computer program components. The one or more computer program components may include one or more of a physicality component, caretaking component, a presentation component, a sensor component, a determination component, and/or other components.

The physicality component may be configured to determine a physical requirement of a user. Custom caretaking information may be determined based on the physical requirement of the user. The physical requirement of the user may be based on a fitness plan for the user.

The caretaking component may be configured to obtain caretaking information for the physical object.

The presentation component may be configured to effectuate presentation of the individual criteria included in the set of caretaking criteria via one or more output devices of the physical object to elicit the physical activity of the user. By way of non-limiting illustration, the presentation component may be configured to effectuate presentation of the first criterion.

The sensor component may be configured to obtain output signals from one or more sensors coupled to the physical object. The output signals may convey activity information and/or other information. The activity information may define one or more values of one or more activity attributes of the physical activity of the user. By way of non-limiting illustration, the activity information may define a first value of a first activity attribute, a second value of the first activity attribute, and/or other values of other activity attributes.

The determination component may be configured to determine whether the individual caretaking criteria are satisfied based on the one or more values of the one or more activity attributes. By way of non-limiting illustration, the determination component may be configured to determine whether the first criterion is satisfied based on the first value, the second value, and/or other values.

The presentation component may be configured to, responsive to the individual caretaking criteria being satisfied based on the one or more values of the one or more activity attributes, effectuate presentation of a satisfaction notification via the one or more output devices. By way of non-limiting illustration, responsive to the first criterion being satisfied based on the second value, presentation may be effectuated of a first satisfaction notification.

The presentation component may be configured to responsive to the individual caretaking criteria not being satisfied based on the one or more values of the one or more activity attributes, effectuate presentation of a nonsatisfaction notification via the one or more output devices.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
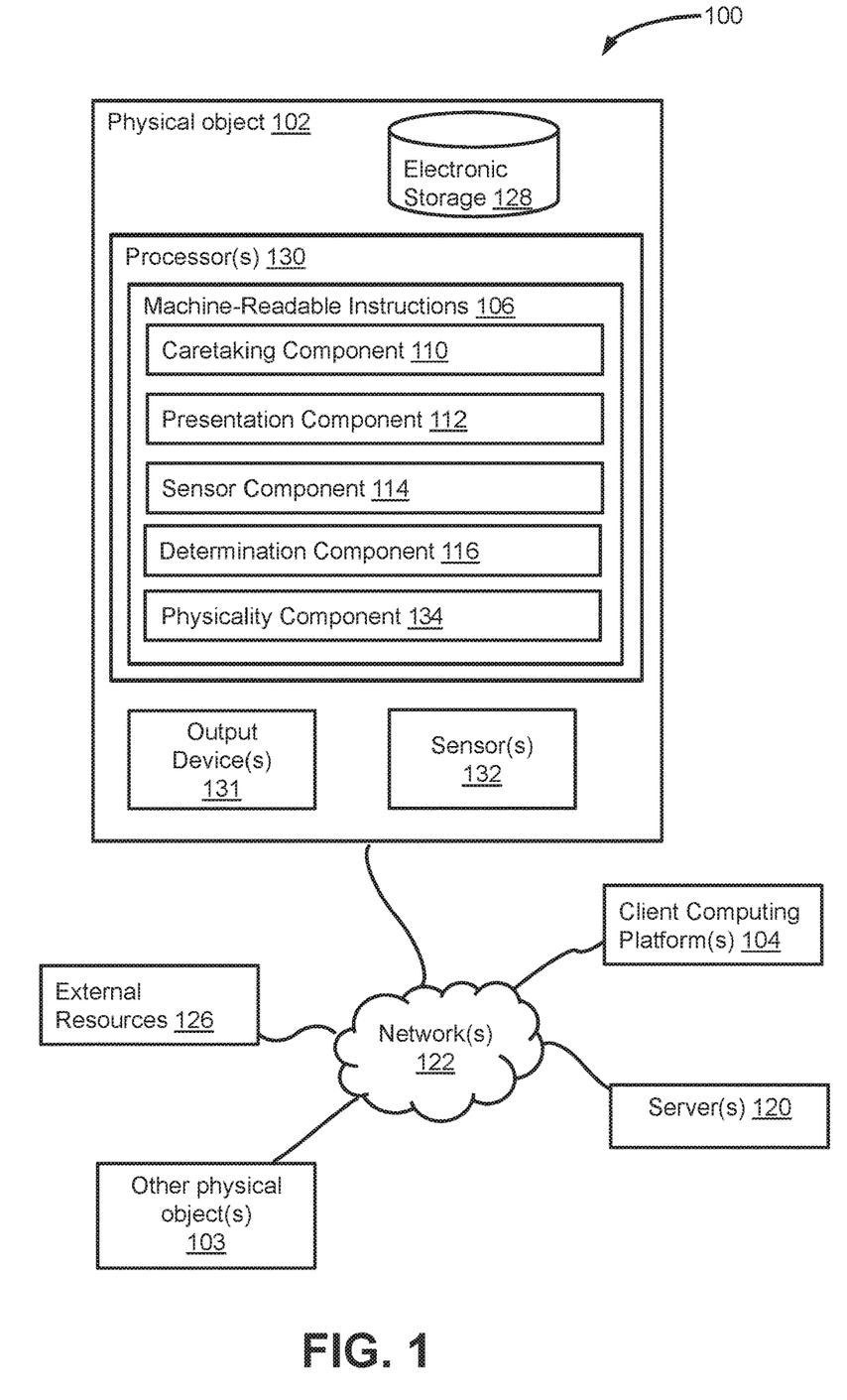
FIG. 1 illustrates a system configured to elicit physical activity in users acting as caretakers of physical objects, in accordance with one or more implementations.

FIG. 1 illustrates a system 100 configured to elicit physical activity in users acting as caretakers of physical objects. The physical object may provide output conveying caretaking requirements for its well-being. The caretaking requirements of the physical object may "trick" the user into performing fitness/wellness behavior in order to satisfying the caretaking requirements even though the caretaking requirements may be unrelated to the fitness/wellness behavior itself. Accordingly, in caring for the physical object, the user may actually be caring for themselves.

In some implementations, system 100 may include one or more of a physical object 102, one or more other physical objects 103, one or more client computing platforms 104, one or more servers 120, one or more external resources 126, and/or other components. It is noted that while one or more features and/or functions of systems and methods presented herein may be directed to physical object 102, this is for illustrative purposes only and not to be considered limiting. For example, other ones of the one or more physical objects 103 may include the same or similar components and/or may be configured in the same or similar manner as physical object 102 described herein.

Physical object 102 may be configured to communicate with one or more client computing platforms 104, one or more servers 120, one or more other physical objects 103, and/or other components of system 100 according to a client/server architecture, peer-to-peer architecture, and/or other architectures. Communications may be facilitated through network(s) 122. The network(s) 122 may include wired and/or wireless connections. The network(s) 122 may include the Internet, Bluetooth, USB, and/or other communication networks. It will be appreciated that this is not intended to be limiting and that the scope of this disclosure includes implementations in which components of system 100 may be operatively linked via some other communication media.

Physical object 102 may include one or more of non-transitory electronic storage 128, one or more physical processors 130 configured by machine-readable instructions 106, one or more output devices 131, one or more sensors 132, and/or other components. In some implementations, physical object 102 may have a form factor of one or more of a toy, a figurine, an article of clothing, and/or other forms. By way of non-limiting illustration, physical object 102 may have be in the form of a plush toy. It is noted that the depiction and description of one or more physical processors 130 configured by machine-readable instructions 106 being included in physical object 102 is for illustrative purposes only and is not to be considered limiting. For example, in some implementations, one or more physical processors 130 may be included in an individual client computing platform and/or individual server. The individual client computing platform and/or individual server may be configured to obtain information from physical object 102 (e.g., output signals from one or more sensors 132) and perform the features and/or functions of machine-readable instructions 106 remotely from physical object 102.

The one or more output devices 131 may include devices configured to provide one or more of visual, auditory, and/or tactile output. An output device may include one or more of a display screen, an audio output device, a tactile output device, and/or other devices. A display screen may be configured to present visual output in the form of one or more of images, video, and/or text. A display screen may include, for example, a liquid-crystal display (LCD) screen and/or other displays screens. An audio output device may be configured to present audio content in the form of words, sounds, and/or other audio content. An audio output device may include, for example, a speaker. A tactile output device may be configured to provide tactile output. A tactile output device may include one or more of a heating element, a vibration motor, and/or other tactile output devices.

Individual sensors of one or more sensors 132 may be configured to generate output signals conveying information usable by system 100 to determine activity of a user. The one or more sensors 132 may include one or more of an image sensor, an orientation sensor, a location sensor, a pressure sensor, a temperature sensor, a light sensor, an audio input sensor, and/or other sensors.

An image sensor may be configured to generate output signals conveying image information. The image information may define visual content in the form of one or more images. Images may be defined by pixels and/or other information. Pixels may be characterized by one or more of pixel location, pixel color, pixel transparency, and/or other information. An image sensor may include one or more of charge-coupled device sensor, active pixel sensor, complementary metal-oxide semiconductor sensor, N-type metal-oxide-semiconductor sensor, and/or other image sensor. The image information may facilitate determination of other information described herein via one or more image-based techniques. By way of non-limiting illustration, techniques may include one or more of computer vision, Speeded Up Robust Features (SURF), Scale-invariant Feature Transform (SIFT), Oriented FAST and rotated BRIEF (ORB), Optical Character Recognition (OCR), facial recognition, and/or other techniques.

In some implementations, an orientation sensor may be configured to generate output signals conveying orientation information and/or other information. Orientation information derived from output signals of an orientation sensor may define an orientation of physical object 102. In some implementations, orientation may refer to one or more of a pitch angle, a roll angle, a yaw angle, heading, pointing direction, and/or other measurements. An orientation sensor may include an inertial measurement unit (IMU) such as one or more of an accelerometer, a gyroscope, a magnetometer, Inclinometers, Electronic nose, Infrared Imagers, Micro-bolometers, micro-displays (DMD), Digital micro-mirror device, Optical Switches, and/or other devices.

In some implementations, a location sensor may be configured to generate output signals conveying location information and/or other information. Location information derived from output signals of a location sensor may define one or more of a geo-location of the physical object 102, an elevation of physical object 102, and/or other measurements. A location sensor may include one or more of a GPS, an altimeter, and/or other devices.

A pressure sensor may be configured to generate output signals conveying pressure information and/or other information. Pressure information derived from output signals of a pressure sensor may define a force per unit area imparted to the pressure sensor. A pressure sensor may include one or more of a piezo resistive strain gauge, a capacitive pressure sensor, an electromagnetic pressure sensor, a piezoelectric sensor, a strain-gauge, and/or other pressure sensors.

A temperature sensor may be configured to generate output signals conveying temperature information and/or other information. Temperature information derived from output signals of a temperature sensor may define one or more of a temperature at the temperature sensor, temperature within a threshold range of the temperature sensor, and/or other measure of temperature. A temperature sensor may include one or more of a thermocouple, a resistive temperature Measuring devices, an infrared sensor, a bimetallic device, a thermometer, and/or other temperature sensors.

A light sensor may be configured to generate output signals conveying ambient light information and/or other information. The ambient light information derived from output signals of a light sensor may define intensity and/or presence (or absence) of light or other electromagnetic radiation incident on the light sensor. A light sensor may include one or more of a photodiode, an active-pixel sensor, photovoltaic, and/or other sensors.

An audio input sensor may be configured to receive audio input. An audio input sensor may include a sound transducer and/or other sensor configured to convert sound (e.g., air pressure variation) into an electrical signal. By way of non-limiting illustration, an audio input sensor may include a microphone.

The non-transitory electronic storage 128 may be configured to store one or more of caretaking information, environment information, and/or other information.

Caretaking information may define a set of caretaking criteria of physical object 102 and/or other information. The individual caretaking criteria may specify one or more caretaking requirements of the physical object 102 which are to be satisfied based on physical activity of a user. The physical activity may be expressed as individual values of individual activity attributes, discussed herein. The caretaking information may further define associations between individual criteria and individual values of individual activity attributes which satisfy the individual criteria, described herein. The associations may be determined based on the environment information, described herein. By way of non-limiting illustration, the set of caretaking criteria may include a first criterion and/or other criteria. The first criterion may be associated with one or more values of a first activity attribute and/or other values of other attributes.

The environment information may define a context of a real-world environment surrounding one or more users. The context of the real-world environment may describe a local environment in which individual users may be present. By way of non-limiting illustration, the context of a real-world environment may include one or more of a mapping of the environment, identification of objects physically present in and/or moving through the environment, locations of the objects physically present in and/or moving through the environment, and/or other information describing the real-world environment. The mapping of the environment may include one or more of physical dimensions of the environment, layout (e.g., roadways, navigation ways, bike paths, walking paths, and/or other information), and/or other information. The objects physically present in the real-world environment may refer to one or more of buildings, points of interest, people, plants, animals, and/or other objects. The environment information may be used to derive additional information about the environment including one or more of locations of objects, distance between objects and/or points of interest, and/or other information which may be derived from the environment information.

In some implementations, the environment information may be derived from one or more external resources 126 and/or other determined in other ways. By way of non-limiting illustration, environment information may be derived from satellite imagery available through, for example, Google® Maps and/or derived from other sources.

In some implementations, the associations between individual criteria and individual values of individual activity attributes which satisfy the individual criteria may be determined based on the environment information, and/or other information. For example, the environment information may provide a causal link between satisfaction of the caretaking criteria and physical activity. This causal link will be described in more detail below with reference to individual ones of the caretaking requirements specified by the individual criteria.

In some implementations, individual criteria may specify one or more of a feeding requirement, a play requirement, a temperature requirement, a rest requirement, swimming requirement, dancing requirement (e.g., duet routine with the caretaker), stretching requirement (e.g., physical object 102 feeding on an apple on a tall branch), socialization requirement (e.g., needs to meet with friends that requires caretaker to walk to different locations), bathroom requirement (e.g., needs to use the bathroom quickly, causing the caretaker to run home within a time limit) and/or other caretaking requirements of the physical object 102 which are to be satisfied based on physical activity of a user.

A feeding requirement may refer to a simulated need of the physical object 102 to intake nourishment. The feeding requirement may be associated with one or more of an identification of food to be consumed, identification of location of the food, and/or other information. In some implementations, food which physical object 102 may "consume" may be associated with individual objects physical present in a real-world environment of a user (and conveyed by the environment information). Satisfaction of a criterion specifying the feeding requirement may be accomplished by bringing the physical object 102 to and/or within a threshold distance of the individual objects so as to give the physical object 102 "access" to the "food" for "consumption." Accordingly, satisfaction of the feeding requirement may require a user to physically move to the location of the object designated as the physical object's food.

A play requirement may refer to a simulated need of the physical object 102 to interact with objects, people, other physical objects, and/or other entities in the real-world. The play requirement may be associated with one or more of an identification of "friends" (e.g., objects, people, other physical objects, and/or other entities) to interact with, types of play, and/or other information. In some implementations, the locations of the objects, people, other physical objects, and/or other entities may be conveyed by the environment information. Satisfaction of a criterion specifying the play requirement may be accomplished by bringing the physical object 102 to and/or within a threshold distance of the individual objects so as to give the physical object 102 "access" to the entity with which it may play. Accordingly, satisfaction of the play requirement including interacting with a "friend" may require a user to physically move to the location of the object designated as the physical object's play "friend." Types of play may be associated with different activities and/or movement that may "entertain" the physical object 102. The types of play may include one or more of being tossed in the air, swung on a swing, spun around, and/or other activities and/or movement that may be considered entertaining. Accordingly, satisfaction of the play requirement including being "tossed in the air" type of play (or other type of play) may require a user to physically toss the physical object 102 one or more times (or perform other actions) thereby exerting energy in a sort of beneficial physical activity to the user.

A temperature requirement may refer to a simulated need of the physical object 102 to be cooled down and/or warmed up. The temperature requirement may be associated with one or more of taking physical object 102 to a cool location, taking physical object 102 to a warm location, personally cooling off physical object 102, and/or other information. In some implementations, cool and/or warm may be associated with individual objects physically present in a real-world environment and/or locations in the real-world where temperature may be known and/or estimated (and conveyed by the environment information). Satisfaction of a criterion specifying the temperature requirement may be accomplished by bringing the physical object 102 to and/or within a threshold distance of the individual objects and/or individual locations so as to give the physical object 102 "access" to the warm and/or cool temperature. Accordingly, satisfaction of the temperature requirement may require a user to physically move to the location of the objects and/or locations thereby exerting energy in a sort of beneficial physical activity to the user. In some implementations, satisfaction of a criterion specifying personally cooling off physical object 102 may be accomplished by blowing on physical object 102. Accordingly, satisfaction of the temperature requirement may require a user to perform one or more breathing exercises with air being directed at physical object 102 thereby exerting energy in a sort of beneficial physical activity to the user.

A rest requirement may refer to a simulated need of the physical object 102 to be still, be in a silent place, and/or otherwise rest. The rest requirement may be associated with one or more of taking physical object 102 to a resting and/or quite location, keeping physical object 102 still, and/or other information. In some implementations, a resting location may be associated with individual objects physically present in a real-world environment and/or locations in the real-world where rest may take place (and conveyed by the environment information). Satisfaction of a criterion specifying the rest requirement may be accomplished by bringing the physical object 102 to and/or within a threshold distance of the individual objects and/or individual locations so as to give the physical object 102 "access" to the rest location. Accordingly, satisfaction of the rest requirement may require a user to physically move to the location of the objects and/or locations thereby exerting energy in a sort of beneficial physical activity to the user. In some implementations, satisfaction of a criterion specifying keeping physical object 102 still may be accomplished by the user holding the physical object 102 without moving. Accordingly, satisfaction of the rest requirement may require a user to hold a pose (e.g., a yoga pose, performing meditation, etc.) thereby either exerting energy in a sort of beneficial physical activity to the user and/or conserving energy in a sort of beneficial activity.

It is noted that the above descriptions of various caretaking requirements are provided for illustrative purposes and is not to be considered limiting. Instead, those skilled in the art may appreciate other caretaking requirements that may be satisfied based on physical activity of a user which are within the scope of this disclosure.

Executing the machine-readable instructions 106 may cause one or more physical processors 130 to facilitate eliciting physical activity in users acting as caretakers of physical objects. Machine-readable instructions 106 may include one or more computer program components. The computer program components may include one or more of a physicality component 134, caretaking component 110, a presentation component 112, a sensor component 114, a determination component 116, and/or other computer program components.

The physicality component 134 may be configured to determine a physical requirement of a user. The physical requirement of the user may be based on a fitness plan for the user. The fitness plan may include various levels of activity required of the user at specified points in time. The fitness plan may include heartrate goals, body weight goals, cardio goals, and/or other physicality goals the user may desire to achieve long term and/or at a specified point in time. Custom caretaking information for physical object 102 may be determined based on the physical requirement of the user (i.e., the fitness plan) determined.

Physicality component 134 may communicate the custom caretaking information for physical object 102 to physical object 102. The custom caretaking information may define a custom set of caretaking criteria of physical object 102. The individual caretaking criteria may specify one or more caretaking requirements of the physical object 102 which are to be satisfied based on values of individual activity attributes. The activity attributes may be customized for the user, and therefore the one or more caretaking requirements, based on the physical requirement of the user determined.

Physicality component 134 may be configured to determine the physical requirement of the user by user input via client computing platform(s) 104, health tracking applications, medical instructions, and/or other methods.

The caretaking component 110 may be configured to obtain caretaking information for the physical object 102 and/or other information. The caretaking information may define a set of caretaking criteria of the physical object 102.

The presentation component 112 may be configured to effectuate presentation of the individual criteria included in the set of caretaking criteria via one or more output devices 131 of the physical object 102 to elicit the physical activity of a user of physical object 102. By way of non-limiting illustration, the presentation component 112 may be configured to effectuate presentation of the first criterion and/or other criteria. In some implementations, presentation of the individual criteria may include conveying the individual criteria via one or more of visual, auditory, and/or tactile output. By way of non-limiting illustration, a display screen may display text, image, and/or video conveying the individual criteria (e.g., display of "I am hungry for apples from the apple tree"). By way of non-limiting illustration, a speaker may reproduce a simulated voice of the physical object 102 conveying the individual criteria. By way of non-limiting illustration, a vibration motor may be activated to convey individual criteria.

The sensor component 114 may be configured to obtain output signals from one or more sensors 132 coupled to the physical object 102. The output signals may convey activity information and/or other information. The activity information may define one or more values of one or more activity attributes of the physical activity of the user. By way of non-limiting illustration, the activity information may define a first value of a first activity attribute, a second value of the first activity attribute, and/or other values of other activity attributes.

An activity attribute may include one or more of a running attribute, a walking attribute, a breathing attribute, a lifting attribute, a quietness attribute, a stillness attribute, and/or other attributes.

A value of a running attribute may specify one or more of a speed at which a user ran, a distance a user ran, a starting location, an ending location, and/or other information. A value of a running attribute may be determined from location information derived from output signals generated by a location sensor and/or other sensor of the physical object 102. By way of non-limiting illustration, location information may indicate that a user has traversed from a starting location to an ending location, a distance therebetween, a time duration, and/or a speed of traversal.

A value of a walking attribute may specify one or more of a speed at which a user walked, a distance a user walked, a starting location, an ending location, and/or other information. A value of a walking attribute may be determined from location information derived from output signals generated by a location sensor and/or other sensor of the physical object 102. By way of non-limiting illustration, location information may indicate that a user has traversed from a starting location to an ending location, a distance therebetween, a time duration, and/or a speed of traversal.

A value of a breathing attribute may specify one or more of an amount of air pressure incident on physical object 102, a duration over which a certain amount of air pressure was incident on physical object 102, and/or other information. A value of a breathing attribute may be determined from pressure information derived from output signals generated by a pressure sensor and/or other sensor of the physical object 102. By way of non-limiting illustration, pressure information may indicate that a user has blown air at a predetermined pressure and/or for a predetermined about of time into physical object 102.

A value of a lifting attribute may specify one or more of an elevation of physical object 102, a change in elevation of physical object 102, a quantity of occurrences of achieving a particular elevation, and/or other information. A value of a lifting attribute may be determined from location information derived from output signals generated by a location sensor and/or other sensor of the physical object 102. By way of non-limiting illustration, location information may indicate that a user has thrown physical object 102 into the air to a certain elevation, for a certain number of times, and/or has achieved a certain elevation change.

A value of a quietness attribute may specify one or more of a sound level measurement (e.g., decibel) of an ambient environment of the physical object 102, a duration over which a sound level measurement was recorded, and/or other information. A value of a quietness attribute may be determined from sound information derived from output signals generated by an audio input sensor and/or other sensor of the physical object 102. By way of non-limiting illustration, sounds information may indicate that a user maintained a certain level of quietness surrounding the physical object 102.

A value of a stillness attribute may specify one or more of an amount of movement of physical object 102, a duration over which an amount of movement was present, and/or other information. A value of a stillness attribute may be determined from orientation information derived from output signals generated by an orientation sensor and/or other sensor of the physical object 102. By way of non-limiting illustration, orientation information may indicate that a user remained still such that there may have been little to no change in orientation of the physical object 102 over a period of time.

It is noted that the above descriptions of various activity attributes and/or their values are provided for illustrative purposes and is not to be considered limiting. Instead, those skilled in the art may appreciate other activity attributes and/or expressions of values of activity attributes which are within the scope of this disclosure.

The determination component 116 may be configured to determine whether the individual caretaking criteria are satisfied based on the one or more values of the one or more activity attributes. By way of non-limiting illustration, the determination component 116 may be configured to determine whether the first criterion is satisfied based on the first value, the second value, and/or other values.

As mentioned above the caretaking information may define associations between individual criteria and individual values of individual activity attributes which satisfy the individual criteria. The associations may be determined based on the environment information. The first criterion may be associated with one or more values of a first activity attribute and/or other values of other attributes. The first criterion may be associated with the second value and not the first value of the first activity attribute by virtue of the context of the real-world environment surrounding the user conveyed by the environment information.

By way of non-limiting illustration, as mentioned above satisfaction of a criterion specifying a feeding requirement may be accomplished by bringing the physical object 102 to and/or within a threshold distance of the individual objects so as to give the physical object 102 "access" to the "food" for "consumption." Accordingly, satisfaction of the feeding requirement may require a user to physically move to the location of the object designated as the physical object's food. Stated otherwise, a criterion specifying a feeding requirement may be associated with a value of a running and/or walking attribute including one or more of a distance equal to a distance between the user and location of the object designated as the physical object's food, an ending location being location of the object designated as the physical object's food, and/or other values. In one implementation, physical object 102 may maintain hunger until criterion is satisfied. If a value of a running and/or walking attribute is an associated value, then it may be determined the criterion is satisfied. If a value of a running and/or walking attribute is not an associated value, then it may be determined the criterion is not satisfied.

By way of non-limiting illustration, as mentioned above satisfaction of the play requirement including being "tossed in the air" type of play (or other type of play) may require a user to physically toss the physical object 102 one or more times (or perform other actions) thereby exerting energy in a sort of beneficial physical activity to the user. Stated otherwise, a criterion specifying a play requirement may be associated with a value of a lifting attribute including one or more of an elevation of physical object 102, a change in elevation of physical object 102, a quantity of occurrences of achieving a particular elevation, and/or other information. If a value of a lifting attribute is an associated value, then it may be determined the criterion is satisfied. If a value of a lifting g attribute is not an associated value, then it may be determined the criterion is not satisfied.

By way of non-limiting illustration, as mentioned above satisfaction of a criterion specifying a temperature requirement may be accomplished by bringing the physical object 102 to and/or within a threshold distance of the individual objects and/or individual locations so as to give the physical object 102 "access" to the warm and/or cool temperature. Stated otherwise, a criterion specifying a temperature requirement may be associated with a value of a running and/or walking attribute including one or more of a distance equal to a distance between the user and location of the object designated as the warm and/or cool temperature location, an ending location being location of the object designated as the warm and/or cool temperature location, and/or other values. If a value of a temperature attribute is an associated value, then it may be determined the criterion is satisfied. If a value of a temperature attribute is not an associated value, then it may be determined the criterion is not satisfied.

By way of non-limiting illustration, as mentioned above satisfaction of a criterion specifying personally cooling off physical object 102 may be accomplished by blowing on physical object 102. Accordingly, satisfaction of the temperature requirement may require a user to perform one or more breathing exercises with air being directed at physical object 102 thereby exerting energy in a sort of beneficial physical activity to the user. Stated otherwise, a criterion specifying a temperature requirement may be associated with a value of a breathing attribute including one or more of an amount of air pressure incident on physical object 102, a duration over which a certain amount of air pressure was incident on physical object 102, and/or other information. If a value of a temperature attribute is an associated value, then it may be determined the criterion is satisfied. If a value of a temperature attribute is not an associated value, then it may be determined the criterion is not satisfied.

By way of non-limiting illustration, as mentioned above satisfaction of a criterion specifying a rest requirement may be accomplished by bringing the physical object 102 to and/or within a threshold distance of the individual objects and/or individual locations so as to give the physical object 102 "access" to the rest location. Stated otherwise, a criterion specifying a rest requirement may be associated with a value of a running and/or walking attribute including one or more of a distance equal to a distance between the user and location of the object designated as the rest location, an ending location being location of the object designated as the rest location, and/or other values. If a value of a rest attribute is an associated value, then it may be determined the criterion is satisfied. If a value of a rest attribute is not an associated value, then it may be determined the criterion is not satisfied.

By way of non-limiting illustration, as mentioned above satisfaction of a criterion specifying keeping physical object 102 still may be accomplished by the user holding the physical object 102 without moving. Accordingly, satisfaction of the rest requirement may require a user to hold a pose (e.g., a yoga pose, performing meditation, etc.) thereby either exerting energy in a sort of beneficial physical activity to the user and/or conserving energy in a sort of beneficial activity. Stated otherwise, a criterion specifying a rest requirement may be associated with a value of a stillness and/or quietness attribute including one or more of an amount of movement of physical object 102, a duration over which an amount of movement was present, a sound level measurement (e.g., decibel) of an ambient environment of the physical object 102, a duration over which a sound level measurement was recorded, and/or other values. If a value of a rest attribute is an associated value, then it may be determined the criterion is satisfied. If a value of a rest attribute is not an associated value, then it may be determined the criterion is not satisfied.

The presentation component 112 may be configured to, responsive to the individual caretaking criteria being satisfied based on the one or more values of the one or more activity attributes, effectuate presentation of one or more satisfaction notification via the one or more output devices 131. By way of non-limiting illustration, responsive to the first criterion being satisfied based on the second value, presentation may be effectuated of a first satisfaction notification.

The presentation component 112 may be configured to, responsive to the individual caretaking criteria not being satisfied based on the one or more values of the one or more activity attributes, effectuate presentation of a nonsatisfaction notification via the one or more output devices.

The caretaking component 110 may be configured to, responsive to the individual caretaking criteria being satisfied based on the one or more values of the one or more activity attributes, obtain additional criteria for the set of caretaking criteria. In this sense, additional caretaking criteria may be "unlocked" based on satisfaction of prior criteria.

Figure 3:
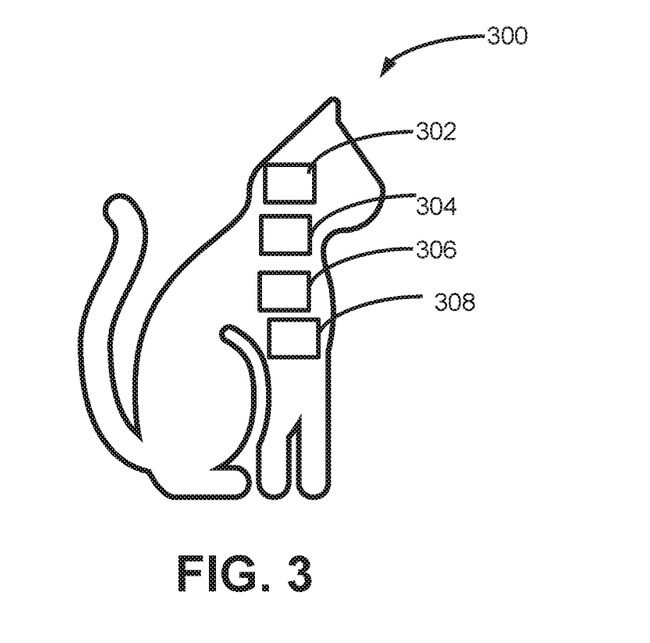
FIG. 3 shows a physical object, in accordance with one or more implementations.

FIG. 3 shows a physical object 300, in accordance with one or more implementations. Physical object 300 may include one or more of non-transitory electronic storage 302, one or more physical processors 304, one or more output devices 306, one or more sensors 308, and/or other components. In some implementations, physical object 300 may have a form factor of one or more of a toy, a figurine, an article of clothing, and/or other forms. By way of non-limiting illustration, physical object 300 may have be in the form of a plush toy. In the illustration of FIG. 3, physical object 300 resembles a plush toy depicting a cat.

Figure 4:
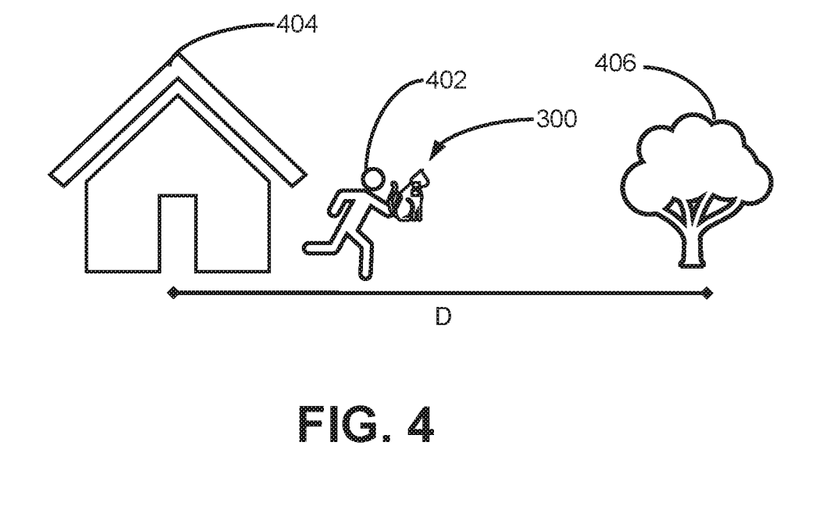
FIG. 4 shows a user performing physical activity in satisfaction of caretaking criteria of a physical object, in accordance with one or more implementations.

FIG. 4 shows a user 402 performing physical activity in satisfaction of caretaking criteria of physical object 300, in accordance with one or more implementations. The caretaking criteria may be presented via one or more output devices of the physical object 300. The caretaking criteria may comprise a caretaking requirement of feeding the physical object 300. The criteria may specify a plant 406 as a food to feed the physical object 300. The caretaking criteria may be satisfied based on physical activity of the user 402. By way of non-limiting illustration, environment information may include information such as a known distance, "D" between a house 404 of the user 402 and the plant 406. The criteria may be satisfied based on output signals from one or more sensors coupled to the physical object 300 conveying activity information. The activity information may convey whether the user has traveled the distance D. In some implementations, the traveling may require a certain speed, timing, or other aspects of the aspects of the activity. Responsive to the activity information conveying the user traveled the distance D, the criteria may be determined to be satisfied. Responsive to the activity information conveying the user has not traveled the distance D, the criteria may be determined to be not satisfied.

Figure 5:
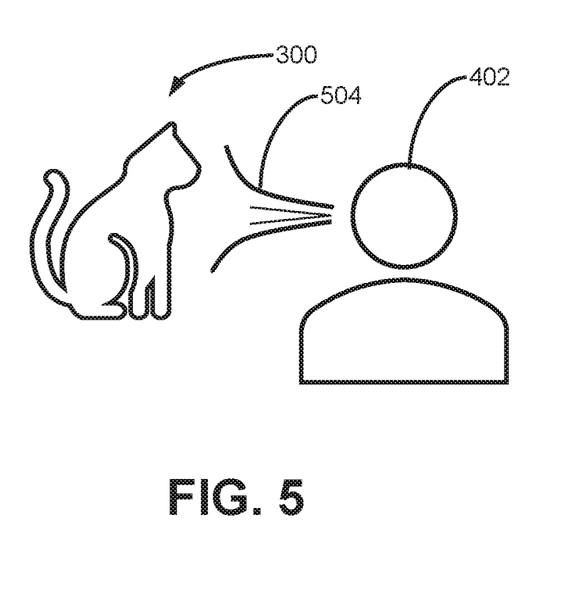
FIG. 5 shows a user performing physical activity in satisfaction of caretaking criteria of a physical object, in accordance with one or more implementations.

FIG. 5 shows user 402 performing physical activity in satisfaction of caretaking criteria of physical object 300, in accordance with one or more implementations. The caretaking criteria may be presented via one or more output devices of the physical object 300. The caretaking criteria may comprise a caretaking requirement of cooling off the physical object 300. The caretaking criteria may be satisfied based on physical activity of the user 402. The criteria may be satisfied based on output signals from one or more sensors coupled to the physical object 300 conveying activity information. The activity information may convey the user has blown air 504 on the physical object 300. In some implementations, the blowing of air 504 may require a certain speed, timing, pressure, duration, or other aspects of the aspects of the activity of blowing. Responsive to the activity information conveying the user blown air 504, the criteria may be determined to be satisfied. Responsive to the activity information conveying the user has not blown air 504, the criteria may be determined to be not satisfied.

Returning to FIG. 1, in some implementations, physical object 102, one or more other physical objects 103, client computing platform(s) 104, server(s) 120, and/or external resources 126 may be operatively linked via one or more electronic communication links. For example, such electronic communication links may be established, at least in part, via a network such as the Internet, Bluetooth, and/or other networks. It will be appreciated that this is not intended to be limiting, and that the scope of this disclosure includes implementations in which physical object 102, one or more other physical objects 103, client computing platform(s) 104, server(s) 120, and/or other components may be operatively linked via some other communication media.

A given client computing platform of one or more client computing platforms 104 may include one or more processors configured to execute computer program components. The computer program components may be configured to enable an expert or user associated with the given client computing platform to interface with system 100 and/or external resources 126, and/or provide other functionality attributed herein to client computing platform(s) 104. By way of non-limiting example, the given client computing platform may include one or more of a desktop computer, a laptop computer, a handheld computer, a tablet computing platform, a NetBook, a Smartphone, a gaming console, and/or other computing platforms. An individual client computing platform's access to system 100 may include accessing one or more of a set of caretaking criteria of physical object 102, indications of individual criteria which have been satisfied and those that have not, and/or other information. A user may be able to select, modify, and/or delete information, for example, individual criteria. By way of non-limiting illustration, one or more user interfaces may be presented on the individual client computing platforms to present information.

External resources 126 may include sources of information outside of system 100, external entities participating with system 100, and/or other resources. In some implementations, some or all of the functionality attributed herein to external resources 126 may be provided by resources included in system 100.

Physical object 102 may include electronic storage 128, one or more processors 130, and/or other components. Physical object 102 may include communication lines, or ports to enable the exchange of information with a network and/or other computing platforms. Illustration of one or more processors 130 in FIG. 1 is not intended to be limiting. The one or more processors 130 may include a plurality of hardware, software, and/or firmware components operating together to provide the functionality attributed herein to one or more processors 130. For example, one or more processors 130 may be implemented by a cloud of computing platforms operating together as one or more processors 130.

Electronic storage 128 may comprise non-transitory storage media that electronically stores information. The electronic storage media of electronic storage 128 may include one or both of system storage that is provided integrally (i.e., substantially non-removable) with one or more processors 130 and/or removable storage that is removably connectable to one or more processors 130 via, for example, a port (e.g., a USB port, a firewire port, etc.) or a drive (e.g., a disk drive, etc.). Electronic storage 128 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 128 may include one or more virtual storage resources (e.g., cloud storage, a virtual private network, and/or other virtual storage resources). Electronic storage 128 may store software algorithms, information determined by processor(s) 130, information received from server(s) 120, information received from client computing platform(s) 104, and/or other information that enables physical object 102 to function as described herein.

Processor(s) 130 may be configured to provide information processing capabilities in server(s) 102. As such, processor(s) 130 may include one or more of a digital processor, an analog processor, a digital circuit designed to process information, an analog circuit designed to process information, a state machine, and/or other mechanisms for electronically processing information. Although processor(s) 130 is shown in FIG. 1 as a single entity, this is for illustrative purposes only. In some implementations, processor(s) 130 may include a plurality of processing units. These processing units may be physically located within the same device, or processor(s) 130 may represent processing functionality of a plurality of devices operating in coordination. Processor(s) 130 may be configured to execute components 110, 112, 114, 116, 134 and/or other components. Processor(s) 130 may be configured to execute components 110, 112, 114, 116, 134 and/or other components by software; hardware; firmware; some combination of software, hardware, and/or firmware; and/or other mechanisms for configuring processing capabilities on processor(s) 130. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 110, 112, 114, 116, and 134 are illustrated in FIG. 1 as being implemented within a single processing unit, in implementations in which processor(s) 130 includes multiple processing units, one or more of components 110, 112, 114, 116, and/or 134 may be implemented remotely from the other components. The description of the functionality provided by the different components 110, 112, 114, 116, and/or 134 described below is for illustrative purposes, and is not intended to be limiting, as any of components 110, 112, 114, 116, and/or 134 may provide more or less functionality than is described. For example, one or more of components 110, 112, 114, 116, and/or 134 may be eliminated, and some or all of its functionality may be provided by other ones of components 110, 112, 114, 116, and/or 134. As another example, processor(s) 130 may be configured to execute one or more additional components that may perform some or all of the functionality attributed below to one of components 110, 112, 114, 116, and/or 134.

Figure 2:
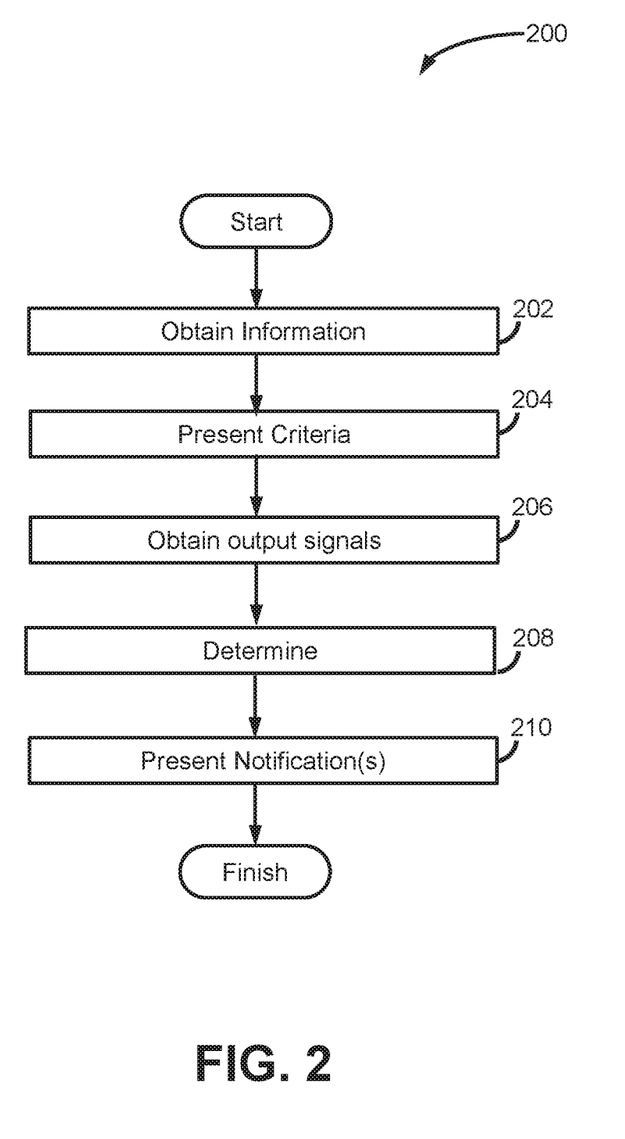
FIG. 2 illustrates a method to elicit physical activity in users acting as caretakers of physical objects, in accordance with one or more implementations

FIG. 2 illustrates a method 200 to elicit physical activity in users acting as caretakers of physical objects, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include obtaining caretaking information defining a set of caretaking criteria of a physical object. The individual caretaking criteria may comprise one or more caretaking requirements of the object to be satisfied based on physical activity of a user. The set of caretaking criteria may include a first criterion. Operation 202 may be performed by one or more hardware processors configured by machine-readable instructions including a component that is the same as or similar to caretaking component 110 (shown in FIG. 1 and described herein).

An operation 204 may include effectuating presentation of the individual criteria included in the set of caretaking criteria via one or more output devices of the physical object to elicit the physical activity of the user. By way of non-limiting illustration, operation 204 may include effectuating presentation of the first criterion. Operation 204 may be performed by one or more hardware processors configured by machine-readable instructions including a component that is the same as or similar to presentation component 112 (shown in FIG. 1 and described herein).

An operation 206 may include obtaining output signals from one or more sensors coupled to the object. The output signals may convey activity information. The activity information may define one or more values of one or more activity attributes of the physical activity of the user. By way of non-limiting illustration, the activity information may define one or more of a first value of a first activity attribute, a second value of the first activity attribute, and/or other values. Operation 206 may be performed by one or more hardware processors configured by machine-readable instructions including a component that is the same as or similar to sensor component 114 (shown in FIG. 1 and described herein).

An operation 208 may include determining whether the individual caretaking criteria are satisfied based on the one or more values of the one or more activity attributes, including determining whether the first criterion is satisfied based on the first value, r the second value, and/or other values. Operation 208 may be performed by one or more hardware processors configured by machine-readable instructions including a component that is the same as or similar to determination component 116 (shown in FIG. 1 and described herein).

An operation 210 may include, responsive to the individual caretaking criteria being satisfied or not satisfied based on the one or more values of the one or more activity attributes, effectuating presentation of one or more notifications via the one or more output devices. By way of non-limiting illustration, responsive to the individual caretaking criteria being satisfied based on the one or more values of the one or more activity attributes, operation 210 may include effectuating presentation of a satisfaction notification via the one or more output devices. By way of non-limiting illustration, responsive to the first criterion being satisfied based on the second value, presentation may be effectuated of a first satisfaction notification. By way of non-limiting illustration, responsive to the individual caretaking criteria not being satisfied based on the one or more values of the one or more activity attributes, operation 210 may include effectuating presentation of a nonsatisfaction notification via the one or more output devices. Operation 210 may be performed by one or more hardware processors configured by machine-readable instructions including a component that is the same as or similar to presentation component 112 (shown in FIG. 1 and described herein).

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to elicit physical activity in users acting as caretakers of physical objects, the system comprising:

non-transitory electronic storage storing caretaking information, the caretaking information defining a set of caretaking criteria of a physical object, individual caretaking criteria comprising one or more caretaking requirements of the physical object to be satisfied based on physical activity of a user, the set of caretaking criteria including a first criterion;

one or more physical processors configured by machine-readable instructions to:

obtain a fitness plan for the user, the fitness plan specifying various physical fitness goals of the user at specified points in time;

determine the caretaking information based on the fitness plan so that the individual caretaking criteria in the set of caretaking criteria of the physical object specify individual caretaking requirements of the physical object which are to be satisfied based on individual values of individual activity attributes corresponding to the various physical fitness goals at the specified points in time;

effectuate presentation of the individual caretaking criteria included in the set of caretaking criteria of the physical object to elicit the physical activity of the user, including effectuating presentation of the first criterion;

obtain output signals from one or more sensors coupled to the physical object, the output signals conveying activity information, the activity information defining one or more values of one or more activity attributes of the physical activity of the user, such that the activity information defines a first value of a first activity attribute and a second value of the first activity attribute;

determine whether the individual caretaking criteria are satisfied based on the one or more values of the one or more activity attributes, including determining whether the first criterion is satisfied based on the first value or the second value;

responsive to the individual caretaking criteria being satisfied based on the one or more values of the one or more activity attributes, effectuate presentation of a satisfaction notification via the one or more output devices, such that responsive to the first criterion being satisfied based on the second value, effectuate presentation of a first satisfaction notification;

responsive to the individual caretaking criteria not being satisfied based on the one or more values of the one or more activity attributes, effectuate presentation of a nonsatisfaction notification via the one or more output devices;

responsive to the individual caretaking criteria being satisfied based on the one or more values of the one or more activity attributes, obtain additional previously unavailable caretaking criteria for the set of caretaking criteria such that the additional previously unavailable caretaking criteria are unlocked based on satisfaction of prior ones of the individual caretaking criteria, wherein the additional previously unavailable caretaking criteria are to be satisfied based on the physical activity yet to be undertaken by the user as the user progresses to the physical fitness goals; and wherein the one or more activity attributes include a plurality of activity attributes, the plurality of activity attributes including:
- a running attribute, wherein a value of the running attribute specifies one or more of a speed at which the user ran, a distance the user ran, a starting location of running, or an ending location of running;
- a walking attribute, wherein a value of the walking attribute specifies one or more of a speed at which the user walked, a distance the user walked, a starting location of walking, or an ending location of walking;
- a lifting attribute, wherein a value of the lifting attribute specifies one or more of an elevation of the physical object, a change in the elevation of the physical object, or a quantity of occurrences of achieving a particular elevation of the physical object;
- a quietness attribute, wherein a value of the quietness attribute specifies one or both of a sound level measurement of an ambient environment of the physical object or a duration over which a given sound level measurement was recorded;
- a stillness attribute, wherein a value of the stillness attribute specifies one or both of an amount of movement or a duration over which the amount of movement is present; and
- a breathing attribute, wherein a value of the breathing attribute specifies one or both of an amount of air pressure incident on the physical object or a duration over which the amount of air pressure is incident on the physical object.

2. The system of claim 1, wherein the caretaking information further defines associations between the individual criteria and individual values of individual activity attributes which satisfy the individual criteria, such that the first criterion is associated with the second value of the first activity attribute.

3. The system of claim 2, wherein the associations are determined based on environment information, the environment information defining a context of the real-world environment surrounding the user, such that the first criterion is associated with the second value and not the first value of the first activity attribute by virtue of the context of the real-world environment surrounding the user.

4. The system of claim 3, wherein the context of the real-world environment surrounding the user includes distance between objects and/or points of interest present in the real-world environment.

5. The system of claim 1, wherein the first criterion includes one or more of a feeding requirement, a temperature requirement, a play requirement, or a rest requirement.

6. The system of claim 1, wherein the physical object takes a form factor of a toy.

7. The system of claim 1, wherein the set of caretaking criteria are accessible via one or more client computing platforms.

8. The system of claim 1, wherein the one or more physical processors are further configured by the machine-readable instructions such that effectuating presentation of the individual caretaking criteria included in the set of caretaking criteria of the physical object is via one or more output devices of the physical object.

9. A method to elicit physical activity in users acting as caretakers of physical objects, the method comprising:
- obtaining a fitness plan for the user, the fitness plan specifying various physical fitness goals of a user at specified points in time;
- determining caretaking information based on the fitness plan, the caretaking information defining a set of caretaking criteria of a physical object, individual caretaking criteria comprising one or more caretaking requirements of the physical object to be satisfied based on physical activity of a user, the set of caretaking criteria including a first criterion, the caretaking information being determined based on the fitness plan so that the individual caretaking criteria in the set of caretaking criteria of the physical object specify individual caretaking requirements of the physical object which are to be satisfied based on individual values of individual activity attributes corresponding to the various physical fitness goals at the specified points in time;
- effectuating presentation of the individual caretaking criteria included in the set of caretaking criteria of the physical object to elicit the physical activity of the user, including effectuating presentation of the first criterion;
- obtaining activity information conveyed by output signals from one or more sensors coupled to the physical object, the activity information defining one or more values of one or more activity attributes of the physical activity of the user, such that the activity information defines a first value of a first activity attribute and a second value of the first activity attribute;
- determining whether the individual caretaking criteria are satisfied based on the one or more values of the one or more activity attributes, including determining whether the first criterion is satisfied based on the first value or the second value;
- responsive to the individual caretaking criteria being satisfied based on the one or more values of the one or more activity attributes, effectuating presentation of a satisfaction notification via the one or more output devices, such that responsive to the first criterion being satisfied based on the second value, effectuating presentation of a first satisfaction notification;
- responsive to the individual caretaking criteria not being satisfied based on the one or more values of the one or more activity attributes, effectuating presentation of a nonsatisfaction notification via the one or more output devices;
- responsive to the individual caretaking criteria being satisfied based on the one or more values of the one or more activity attributes, obtaining additional previously unavailable caretaking criteria for the set of caretaking criteria such that the additional previously unavailable caretaking criteria are unlocked based on satisfaction of prior ones of the individual caretaking criteria, wherein the additional previously unavailable caretaking criteria are to be satisfied based on the physical activity yet to be undertaken by the user as the user progresses to the physical fitness goals; and wherein the one or more activity attributes include a plurality of activity attributes, the plurality of activity attributes including:
- a running attribute, wherein a value of the running attribute specifies one or more of a speed at which the user ran, a distance the user ran, a starting location of running, or an ending location of running;
- a walking attribute, wherein a value of the walking attribute specifies one or more of a speed at which the user walked, a distance the user walked, a starting location of walking, or an ending location of walking;
- a lifting attribute, wherein a value of the lifting attribute specifies one or more of an elevation of the physical object, a change in the elevation of the physical object, or a quantity of occurrences of achieving a particular elevation of the physical object;
- a quietness attribute, wherein a value of the quietness attribute specifies one or both of a sound level measurement of an ambient environment of the physical object or a duration over which a given sound level measurement was recorded;
- a stillness attribute, wherein a value of the stillness attribute specifies one or both of an amount of movement or a duration over which the amount of movement is present; and
- a breathing attribute, wherein a value of the breathing attribute specifies one or both of an amount of air pressure incident on the physical object or a duration over which the amount of air pressure is incident on the physical object.

10. The method of claim 9, wherein the caretaking information further defines associations between the individual criteria and individual values of individual activity attributes which satisfy the individual criteria, such that the first criterion is associated with the second value of the first activity attribute.

11. The method of claim 10, wherein the associations are determined based on environment information, the environment information defining a context of the real-world environment surrounding the user, such that the first criterion is associated with the second value and not the first value of the first activity attribute by virtue of the context of the real-world environment surrounding the user.

12. The method of claim 11, wherein the context of the real-world environment surrounding the user includes distance between objects and/or points of interest present in the real-world environment.

13. The method of claim 9, wherein the first criterion includes one or more of a feeding requirement, a temperature requirement, a play requirement, or a rest requirement.

14. The method of claim 9, wherein the physical object takes a form factor of a toy.

15. The method of claim 9, providing access to the set of caretaking criteria to one or more client computing platforms.

16. The method of 9, further comprising:
effectuating presentation of the individual caretaking criteria included in the set of caretaking criteria of the physical object via one or more output devices of the physical object.

* * * * *